(12) United States Patent  
Yoshino

(10) Patent No.: US 6,319,235 B1  
(45) Date of Patent: Nov. 20, 2001

(54) SYRINGE SERVING ALSO AS AN AMPULE AND ASSOCIATED EQUIPMENT

(75) Inventor: Koichi Yoshino, 9-2, Izumidai 3-chome Kita-ku, Kobe-shi Hyogo 651-11 (JP)

(73) Assignees: Koichi Yoshino; Kenichi Yoshino; Naomi Yoshino, all of Hyogo (JP)

( * ) Notice: Subject to any disclaimer, the term of this patent is extended or adjusted under 35 U.S.C. 154(b) by 0 days.

(21) Appl. No.: 09/029,332

(22) PCT Filed: Sep. 4, 1996

(86) PCT No.: PCT/JP96/02522

§ 371 Date: Mar. 4, 1998

§ 102(e) Date: Mar. 4, 1998

(87) PCT Pub. No.: WO97/09079

PCT Pub. Date: Mar. 13, 1997

(30) Foreign Application Priority Data

Sep. 8, 1995 (JP) .................................... 7-231266

(51) Int. Cl.[7] .................................. A61M 5/178
(52) U.S. Cl. ............................ 604/216; 604/212
(58) Field of Search .................. 604/181, 182, 604/185–186, 187, 200–201, 212, 214–218, 240–241, 243–244, 256–257; 222/206, 207, 209–213; 239/309, 327–328

(56) References Cited

U.S. PATENT DOCUMENTS 3,557,788 * 1/1971 Swartz .
3,938,514 * 2/1976 Boucher .
4,753,638   6/1988 Peters .
5,002,066 * 3/1991 Simpson et al. .
5,219,338 * 6/1993 Haworth .

FOREIGN PATENT DOCUMENTS 55-62336  4/1980 (JP) .
1-84651   6/1989 (JP) .

* cited by examiner

Primary Examiner—Richard K. Seidel  
Assistant Examiner—LoAn H. Thanh  
(74) Attorney, Agent, or Firm—Jordan and Hamburg LLP

(57) ABSTRACT

A syringe serves also as an ampule and saves labor in transferring contained liquid from an ampule container to a syringe and is not bulky when disposing it. The syringe has a piston integrally molded in a bellows-like cylindrical portion sealingly containing liquid medicine. Pleated reinforcing portions are longitudinally provided at several positions on the bellows portion. Furthermore, retainers are provided to retain a contracted state of the bellows-like cylindrical portion. The piston has a depression formed in a rear portion thereof for pressing by a finger. A needle portion is fitted into the leading end of a cylindrical barrel portion of the bellows. A projection is provided inside the needle portion so as to break a seal sealing liquid medicine and the leading end of the barrel portion of the syringe may be threadingly fitted to a three-way cock for drip infusion.

17 Claims, 4 Drawing Sheets

SYRINGE SERVING ALSO AS AN AMPULE AND ASSOCIATED EQUIPMENT

BACKGROUND OF THE INVENTION

The present invention relates to a syringe serving also as an ampule and a syringe for collecting blood. In particular, the syringe has a bellows-like cylindrical portion and a pleats reinforcement fold, formed by melting, which make the bellows-like cylinder elastically smooth. The present invention also relates to a three-way cock which is applicable to above syringe.

Generally a conventional syringe 21 has the structure that a piston 23 is inserted within a cylinder 22 and a needle portion 24 is put in a tip shown in FIG. 7. In the case of injecting a liquid medicine by this conventional syringe, a neck portion of an ampule including the liquid medicine shown in FIG. 8 has to be cut with a file so that the needle of the syringe 21 sucks up the liquid medicine into the cylinder of the syringe by insertion within the ampule directly.

In this type of ampule enclosed plastics or a cork plug enclose the liquid medicine and the liquid medicine is sucked by inserting the needle of the syringe in the ampule.

At this time it is troublesome to cut the neck of the above ampule. Furthermore the sharp cut surface of the ampules often hurts fingers if it is made of glass. It is very dangerous because the glass ampule may be crushed by earthquake or other displacement force.

The type of ampule sealed by a plug has the problems of choking the needle of the syringe with cork and plastic resin scrap resulting from thrusting the syringe into the sealed cork. This increases infection into the body. The cork also dulls the needle which results in additional pain to a patient. Another problem is that the volume of cork or resin type ampule is large, and using the medicine at more than one occasion may yield infection.

Yet another problem resulting from various kinds of ampules is that when they are put into the syringe, mistakes of picking the ampules are likely to be made. In addition to the danger of injury results from the sharp cut surface of the ampule. And a large amount of empty ampules after use add to the social waste problem.

The problem has occurred in the waste of conventional syringes. Namely conventional syringes shown in FIG. 7 cannot be smaller than the length X of the needle portion and the length Y of the cylinder and the piston end portion so that conventional syringes are bulky wastes.

SUMMARY OF THE INVENTION

The present invention is made in consideration with the above points at issue. The inventor has completed the present invention after a great deal of experiments and improvements to realize a syringe taking a smaller amount of room by uniting the conventional ampule and the syringe which cannot be shortened into one.

This invention discloses a syringe serving both as an ampule and syringe which has an extruding piston integrally molded in a bellows-like body portion, with a sealing film for enclosing the liquid contents, and a blood collecting syringe having a bellows shape syringe, a bellows-contracted-state retainer and a bellows-expanding grip.

The syringes include a cylindrical portion of the syringe body made of bellows and, to ensure smooth expansion and/or contraction of the bellows-like cylindrical portion, a pleated reinforcing portion is longitudinally provided at several positions by using a melting portion. The syringes include a unit for holding a pressed condition. The syringe is equipped with front and rear wings, and a hook is located on the rear wing to hold the wings together. In addition, a top end of both syringes is conical and includes a piston with a hollow finger pushing portion 9 on the rear portion thereof and a needle portion which can be threadingly fitted to a tip of cylinder body.

The syringe serves also as an ampule has a convex projection inside the needle portion to tear the seal film sealing a content liquid. This syringe serves also as an ampule and can be used as a drip with the top of syringe accommodating a three way cock. And in the collecting syringe, a back wing located at a back portion of the syringe can be used as a holder for stretch bellows.

DETAILED DESCRIPTION OF THE PREFERRED EXAMPLE

Figure 4:
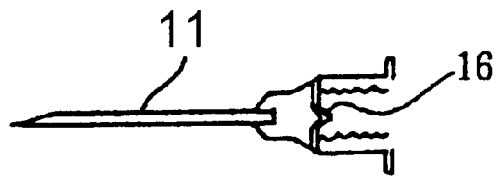
FIG. 4 is a sectional view of a needle portion in accordance with the second example of the present invention.

It is desirable to use a medicine proof plastic like fluorine resin, isophthalic acid type unsaturated polyester resin, vinyl ester resin, epoxy resin and fran resin as material of a syringe of the present invention. As for the corrosion resistance of resin, it is important effect of curing agent. A needle for hypodermic use needs to be sharpened on both sides so as to go through a seal film retaining liquid medicine. In case of using a needle having one side sharp, it is necessary to set an inner projection 16 shown in FIG. 4 to tear the seal film. The projection needle having one sharp side is appropriate for use with a syringe for collecting blood since it does not have the sealing film.

Figure 3:
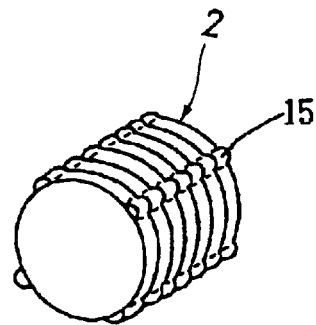
FIG. 3 is a perspective illustration of a bellows-like tube portion with reinforcement gathers in accordance with a second example of the present invention.

It is necessary that some reinforcement gathers 15 shown in FIG. 3 be set on a bellows shape tube portion as a pushing pressure passage. The projections and dents of the gathers shown in FIG. 3 are shaped to be thicker toward an outside surface.

Generally it is an easy method of producing the bellows shape tube portion by molding each half side body and joining both side bodies. At this point of joining, making a side thicker than another portion yield reinforcement gathers. A number of the reinforcement gathers varies with the size and the use of the syringe. The reinforcement gathers help also to prevent bellows bend.

It is possible to join the body portion and the needle portion by molding the diameter of the body portion to be a little smaller than that of the needle portion. Then concerning the joint pattern, it is also acceptable to thrust the body portion into the needle portion with screw cutting.

Liquid medicine is administered in drips through a three way cock by this invention, the tip of syringe being preferably threadingly fitted to the three way cock.

The sealing films 10, 10' are set in an inner tip of the body portion of the syringe to serve as an ampule to enclose the liquid medicine. It is acceptable for a sealing film to be set at the position 10 or 10' in accordance with the invention.

A hollow 9 for pressing by a finger is set at the back of the cylinder.

The projections 7 set on the back wing 6a, 6b are able to be inserted in the inserting hole C, D of the front wing 5a, 5b. And conic head portion 7A, 7B are set at the tip of the projections unless the projections 7 do not come off.

The preferred example of the present invention is described referring to drawings 1 to 6 and 9.

Figure 1A:
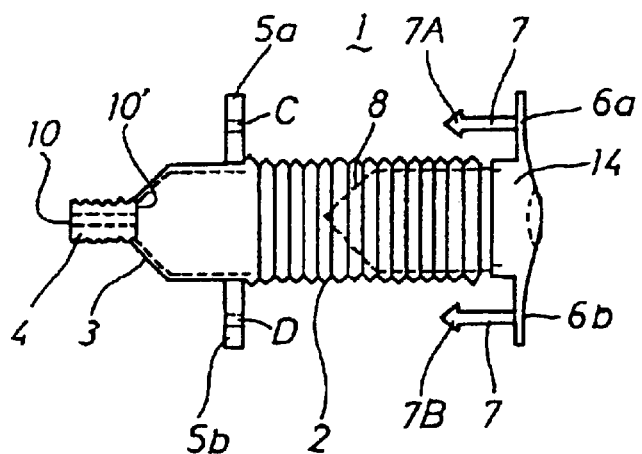
FIG. 1(*a*) is a front view of a body portion of a syringe serving also as an ampule and FIG. 1(*b*) is a right sectional view of the syringe serving also as an ampule in accordance with a first example of the present invention.
Figure 1B:
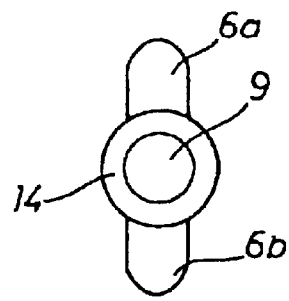

A first example illustrates the syringe serving also as an ampule for injecting liquid medicine. FIG. 1(a) is a front view of the body portion 1 and FIG. 1(b) is a top sectional view of the syringe serving also as an ampule.

Figure 2:
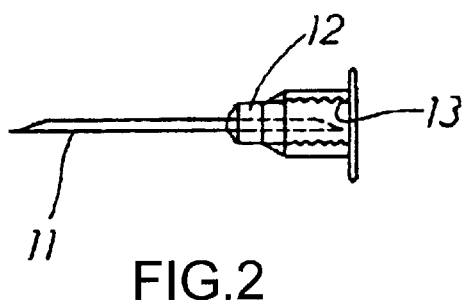
FIG. 2 is a front view of a needle portion in accordance with the first example of the present invention.

A bellows shape tube portion 2 is connected to tip portion 3. A screw shape portion 4 is connected to tip portion 3. Front wings 5a, 5b are connected to tip portion 3. Back wings 6a, 6b are set on a back portion 14 and include projections 7. Piston 8 is integrally molded to bellows shape tube portion 2. Back portion 14 includes a hollow 9 for pressing by a finger. Sealing film 10 seals screw shape portion 4. Sealing film 10' seals tip portion 3. FIG. 2 is a front view of a needle portion. The needle portion includes a taper shape needle 11 on both sides thereof, a cap 12 and a screw shape portion 13 inside the cap.

Portion 1 is made of medicine proof plastic (for example, polypropylene) including the tip portion 3, the bellows shape tube portion 2 and the back finger pushing portion 14 with the piston 8. The front wings 5a, 5b are set on the tip portion 3 and the back wings 6a, 6b set on the back portion 14. The back wings 6a, 6b include a projection 7. The projection 7 has shaft portions and conic head portions 7A, 7B with a larger diameter than the shaft portion. The front wings ia, 5b have inserting holes C, D with the same diameter as the projecting shaft to fit the projection 7.

Other types of projection s a re acceptable in the invention.

Figure 6:
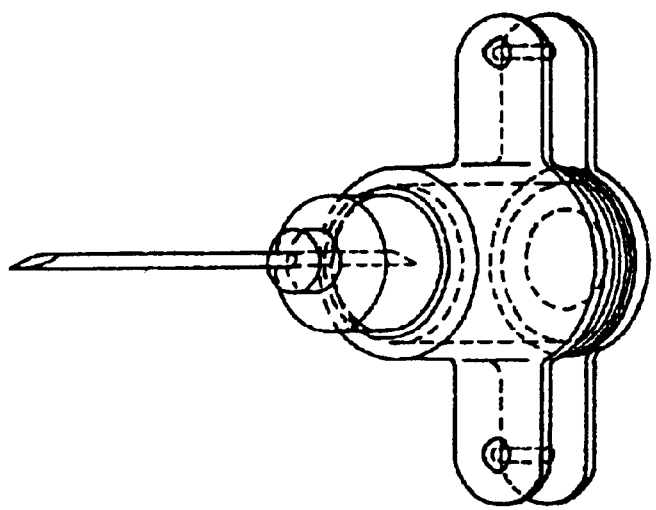
FIG. 6 illustrates the syringe serving in accordance with the first example of the present invention before disposing.
Figure 7:
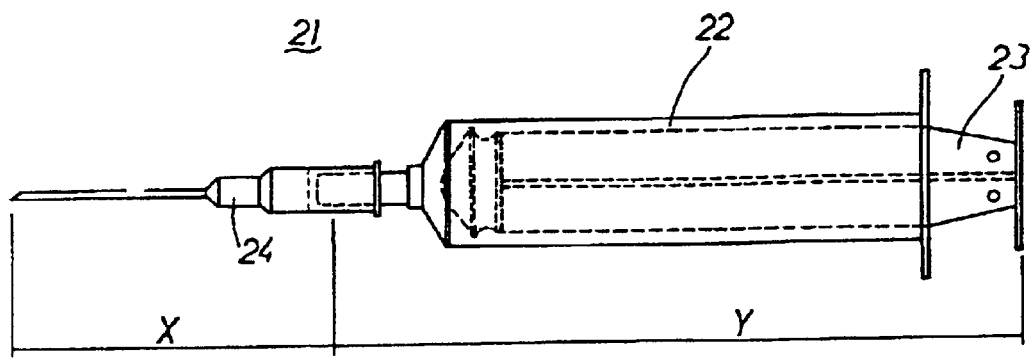
FIG. 7 is a front view of a conventional syringe.
Figure 8:
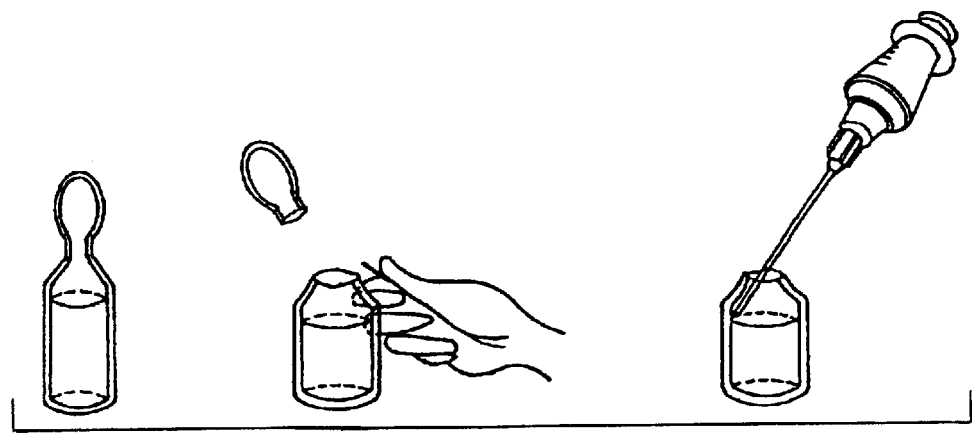
FIG. 8 illustrates a procedure for sucking up the liquid medicine from the conventional ampule.

The bellows 2 stretch because of including the liquid medicine at the beginning of use with the result that the projection 7 is apart from the inserting hole C, D of the front wing 5a, 5b. But after injecting the liquid medicine, the projection 7 is fitted in the inserting hole C, D shown in FIG. 6 to secure the projection 7. The conic head portion 7A, 7B cannot be separated after interfitting because of the shape thereof The syringe of the present invention is very convenient and safe to scrap compactly.

The sealing film 10 set on the most tip portion of the screw shape portion 4 in this example is also able to be set on the inner tip portion 10'.

In a second embodiment, the pleats for reinforcement 15, shown in FIG. 3, are vertically attached at 4 points on the bellows-like cylindrical portion 2 according to the first embodiment. The material of the syringe of this present invention is changed with fluorine resin. Only at the leading end is the needle sharpened and inside projection 16 (FIG. 4) is provided inside the needle portion. Except for the above differences, the syringe is produced in the same way as the first embodiment (FIG. 3).

Thus, the pleats guide against pushing pressure. The syringe of this present invention can be used easily because the pleats provide reinforcement.

Accordingly the number of reinforcement pleats does not matter so much, but 2 to 6 pleats are reasonable. And in this example, the convex inside projection 16 breaks through the sealing film 10 sealing the liquid medicine so the sealing film 10 is broken definitely and largely and the danger of which a broken piece of the sealing film 10 obstructs a hole inside the needle is reduced.

Figure 9:
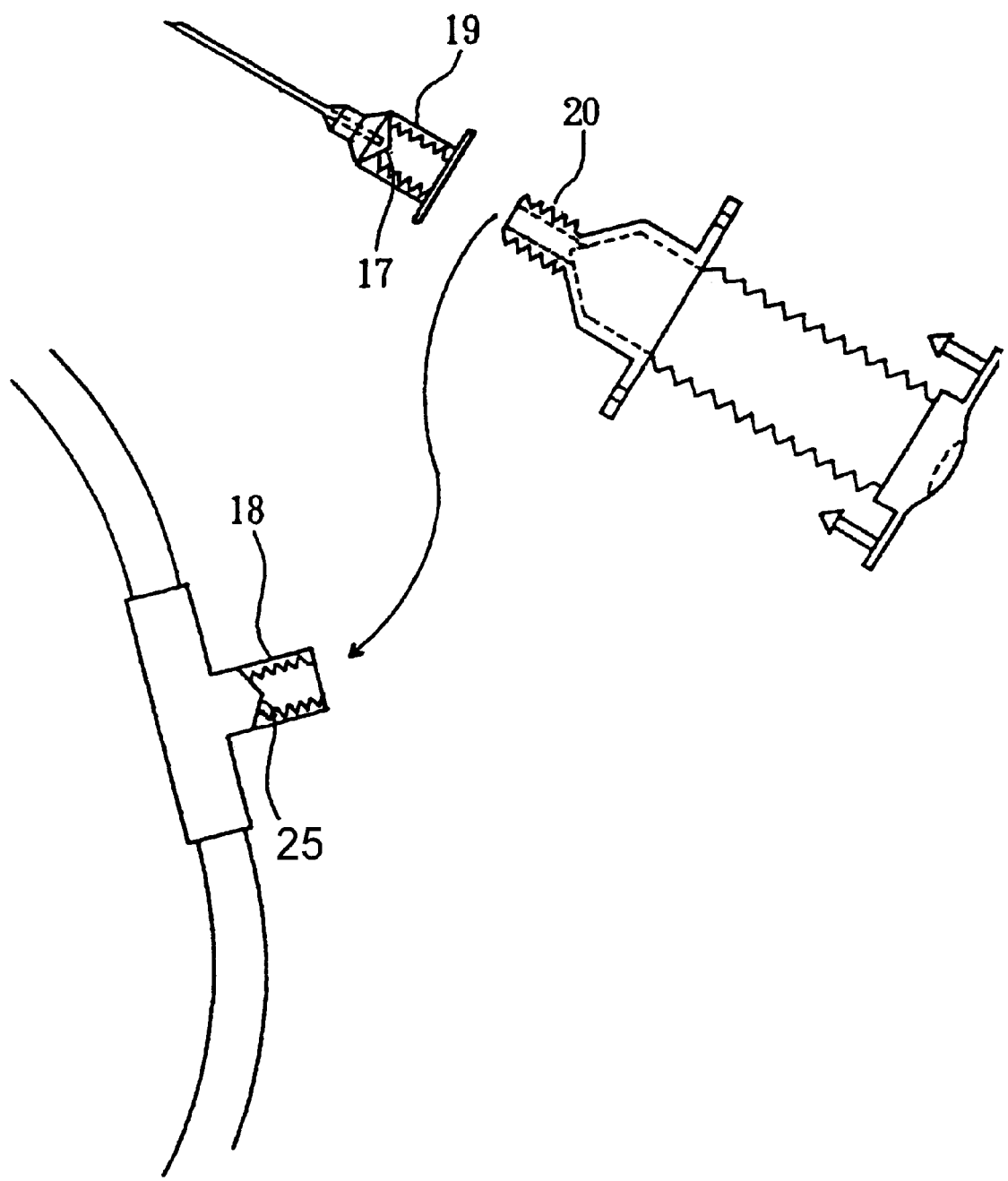
FIG. 9 illustrates operation of a drip infusion in accordance with a third example of the present invention.

Shown in FIG. 9, is a third embodiment, wherein a material of the syringe is altered to isophthalic acid type unsaturated polyester resin, only a tip of the needle is sharpened, an inner projection 17 (FIG. 9) is equipped in the needle portion, and a tip of syringe is made for interfitting to a three way cock 18 of a drip tube.

For adding liquid medicine by drip infusion with this invention, first, the sealing film 10 is torn by interfitting needle portion 19 to a top end of body 20. Second by taking off needle portion 19 again, the top end of the body 20 is interfitted to the three way cock 18. This method of drip style makes it possible to add liquid medicine. To simplify the operation for taking off after interfitting needle portion 19 to the top of the body 20, and for preventing liquid leak, projection 25 for tearing seal film 10 may be equipped inside three way cock 18.

According to above description, wide use is possible in medical situations by matching the shape or diameter with presented equipment.

Figure 5:
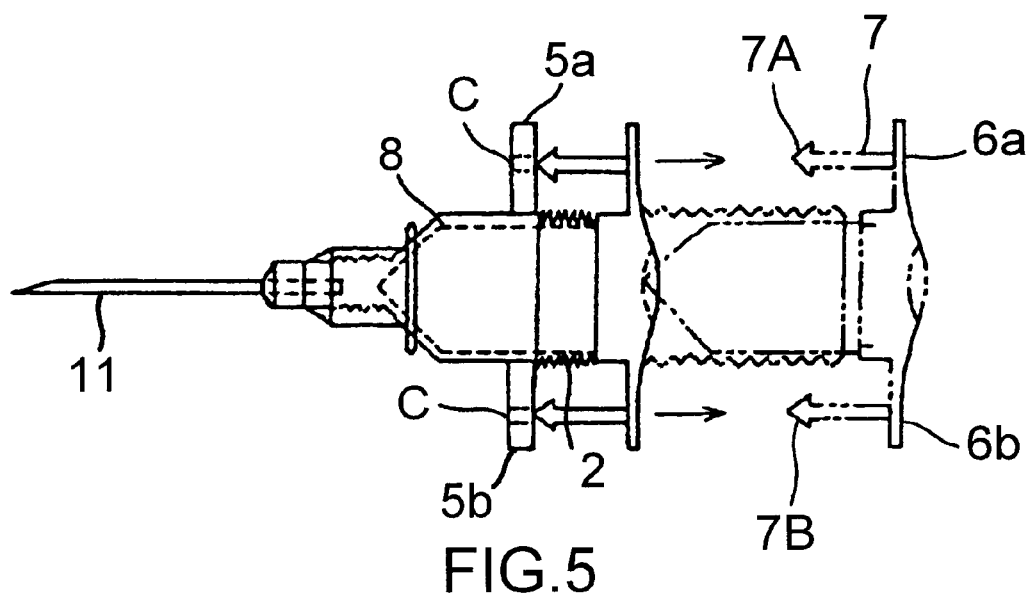
FIG. 5 is a side view of a syringe for collecting blood in accordance with a fourth example of the present invention.

FIG. 5 shows a collecting syringe of a fourth embodiment. In this example, the needle 11 is one side sharpend and an inside of the bellows body 2 is empty with no liquid medicine. A sealing film is not equipped. So that the bellows body 2 is in a contracted state and will save space at the beginning. In case of collecting blood, the piston 8 is pulled in the direction of the arrow of FIG. 5 so blood is drawn in the bellows-like cylinder 2.

The syringe like this is not bulky before collecting blood and after use, for collecting blood the syringe may be pulled releasing the condition of holding by tips 7A, 7B by pulling the piston 8 in the direction of the arrows in FIG. 5 with back wing 6a and front wing 6b as fulcrums.

This syringe can be disposed with interfitting projections 7 into front wing holes C and contracting the bellows body 2 as before when collecting blood is transferred to a test tube.

In the first to fourth embodiments it is possible to join the leading end portion of needle and barrel portion with a simple cap setting type. Furthermore it is possible to form integrally the back pressing finger portion 14 and cylinder. But it is desirable to form integrally them in order to inject liquid medicine and for collecting blood.

As described above, there is no need in this invention of the operation to pull out liquid medicine into syringe and also to cut off the neck of the ampule, to dispose ampule in all types of syringe, as example hypodermic, sarcasm, intramuscular, spread, intravenous. It is impossible to shot at the spot. So injury from an ampule cut end is prevented. In the collecting syringe it is convenient that the shape before use can be compact. The reinforcement make the pull and push operation smooth. And after use syringes can be compacted and are convenient to dispose.

What is claimed is:

1. A syringe device comprising:
   a piston;
   a cylinder portion for accepting said piston therein, said cylinder portion having a tip end;
   said tip end having a frangible seal film; and
   a bellows portion sealingly interconnecting said cylinder portion and said piston in a sealed manner such that said piston is insertable into said cylinder portion and the bellows portion, the piston, and the cylinder portion together form an ampule container for containing a medicinal liquid.

2. The syringe according to claim 1, wherein the bellows portion has half side body portions and the bellows portion is formed by joining together said half side body portions.

3. The syringe according to claim 1, wherein the bellows portion is integrally molded along with the piston.

4. The syringe according to claim 1, wherein the bellows portion includes reinforcement pleats extending in a collapsing and expanding direction of the bellows portion.

5. A syringe device comprising:
   a piston;
   a cylinder portion for accepting said piston therein, said cylinder portion having a tip end;
   said tip end having a frangible seal film and a threaded portion;
   a bellows portion sealingly interconnecting said cylinder portion and said piston in a sealed manner such that said piston is insertable into said cylinder portion and the bellows portion, the piston, and the cylinder portion together form an ampule container for containing a medicinal liquid;
   a needle portion having a needle and accepting said threaded portion of the tip portion; and
   said needle portion having an inside projection for breaking said frangible seal film and thereby communicating said needle with said ampule container for passing medicinal liquid therethrough.

6. The syringe according to claim 5, wherein said needle portion forms a receiving cavity having said inside projection disposed therein and said inside cavity being threaded to accept said threaded portion of said tip portion.

7. The syringe according to claim 5, wherein the bellows portion is integrally molded along with said piston.

8. The syringe according to claim 5, further comprising:
   at least one cylinder wing portion extending from said cylinder portion and defining an aperture; and
   said piston having at least one piston wing portion with a projection for engaging said aperture of said at least one cylinder wing portion to hold said piston at a position within the interior of said cylinder portion.

9. A syringe comprising:
   a piston;
   a cylinder portion for accepting said piston therein, said cylinder portion having a tip end with a channel communicating with an interior of said cylinder portion;
   a bellows portion sealingly interconnecting said cylinder portion and said piston in a sealed manner such that said piston is movable into and out of the interior of said cylinder portion, and the bellows portion, the piston, and the cylinder portion together form a container for receiving a liquid through said channel of said tip end upon withdrawal of said piston from the interior of said cylinder portion;
   at least one cylinder wing portion extending from said cylinder portion and defining an aperture; and
   said piston having at least one piston wing portion with a projection for engaging said aperture of said at least one cylinder wing portion to hold said piston at a position within the interior of said cylinder portion.

10. The syringe according to claim 9, wherein the projection has a conic head portion.

11. The syringe according to claim 9, further comprising a seal in said channel of said tip end which is removable.

12. The syringe according to claim 9, wherein the bellows portion is integrally molded along with the piston.

13. A syringe comprising:
   a piston;
   a cylinder portion for accepting said piston therein, said cylinder portion having a tip end with a channel for communicating with an interior of said cylinder portion;
   a seal occluding said channel;
   a bellows portion sealingly interconnecting said cylinder portion and said piston in a sealed manner such that said piston is movable into and out of the interior of said cylinder portion, and the bellows portion, the piston, and the cylinder portion together form a container for receiving a liquid therein;
   a threaded portion provided on said tip end;
   a needle portion having a needle and accepting said threaded portion of the tip portion; and
   said needle portion having an inside projection for breaking said seal and thereby communicating said needle with said container via said channel for passing liquid therethrough.

14. The syringe according to claim 13, further comprising:
   at least one cylinder wing portion extending from said cylinder portion and defining an aperture; and
   said piston having at least one piston wing portion with a projection for engaging said aperture of said at least one cylinder wing portion to hold said piston at a position within the interior of said cylinder portion.

15. The syringe according to claim 13, where in the bellows portion is integrally molded along with the piston.

16. A syringe device comprising:
   a piston;
   a cylinder portion for accepting said piston therein, said cylinder portion having a tip end;
   said tip end having a frangible seal film; and
   a bellows portion sealingly interconnecting said cylinder portion and said piston in a sealed manner such that said piston is insertable into said cylinder portion and the bellows portion, the piston, and the cylinder portion together form an ampule container for containing a medicinal liquid;
   a threaded portion on said tip end; and
   a three-way cock having a receiving portion for accepting said threaded portion an inside projection for puncturing said frangible seal film.

17. The syringe according to claim 16, wherein the bellows portion is integrally molded to the piston.

* * * * *